(12) United States Patent
Bentwich (10) Patent No.: US 8,805,516 B2
(45) Date of Patent: Aug. 12, 2014

(54) INTEGRATED SYSTEM AND METHOD FOR TREATING DISEASE USING COGNITIVE TRAINING AND BRAIN STIMULATION AND COMPUTERIZED MAGNETIC PHOTOELECTRIC STIMULATOR (CMPES)

(71) Applicant: Neuronix Ltd., Ramat Yishai (IL)

(72) Inventor: Jonathan Bentwich, Hauppauge, NY (US)

(73) Assignee: Neuronix Ltd., Ramat Yishai (IL)

(*) Notice: Subject to any disclaimer, the term of this patent is extended or adjusted under 35 U.S.C. 154(b) by 0 days.

(21) Appl. No.: 13/912,868

(22) Filed: Jun. 7, 2013

(65) Prior Publication Data
US 2013/0267761 A1    Oct. 10, 2013

Related U.S. Application Data (63) Continuation of application No. 12/153,037, filed on May 13, 2008, now Pat. No. 8,498,708, which is a continuation of application No. 10/904,505, filed on Nov. 14, 2004, now abandoned.

(60) Provisional application No. 60/522,286, filed on Sep. 13, 2004.

(51) Int. Cl.
| | |
|---|---|
| *A61N 2/00* | (2006.01) |
| *A61N 1/36* | (2006.01) |
| *A61B 5/00* | (2006.01) |

(52) U.S. Cl.
CPC ........ *A61N 1/36082* (2013.01); *A61N 1/36092* (2013.01); *A61N 2/002* (2013.01); *A61B 5/4088* (2013.01)
USPC .......................................................... 607/45

(58) Field of Classification Search
USPC ......... 607/1–3, 45, 55–57, 89, 100–103, 115, 607/139, 142, 148, 154, 155–156; 600/9, 600/11–15, 544–545
IPC .................... A61N 1/36082, 1/36, 1/0531, 1/40, A61N 1/36025, 1/37, 1/36014, 1/08, 1/36103, A61N 1/00, 1/0529, 1/0526, 1/0408, 1/0472, A61N 1/0484, 1/3606
See application file for complete search history.

(56) References Cited

U.S. PATENT DOCUMENTS

| | | |
|---|---|---|
| 3,890,957 A | 6/1975 | Freeman |
| 4,421,122 A | 12/1983 | Duffy |

(Continued)

FOREIGN PATENT DOCUMENTS

| | | |
|---|---|---|
| WO | 2005/000153 A2 | 1/2005 |
| WO | 2006/044793 A2 | 4/2006 |
| WO | 2007/047854 A2 | 4/2007 |

OTHER PUBLICATIONS

Bennys, et al., "Diagnostic value of quantitative EEG in Alzheimer's disease," Neurophysiol Clin, 31:153-160 (2001).

(Continued)

*Primary Examiner* — Deborah Malamud
(74) *Attorney, Agent, or Firm* — Browdy and Neimark, PLLC (57) ABSTRACT

An integrated system and method for treatment of various diseases, including psychiatric, mental and brain disorders, which preferably combines personalized non-invasive neuronal brain stimulation together with appropriate personalized cognitive training, and which iteratively fine-tunes this treatment by monitoring specific cognitive and brain functions in response to the treatment. A novel brain stimulator device and method, Computerized Magnetic Photo-Electric Stimulator (CCMPES), is described, which integrates electromagnetic stimulation with laser stimulation to generate a magnetic photo-electric stimulation.

7 Claims, 5 Drawing Sheets (56) References Cited

U.S. PATENT DOCUMENTS

| | | |
|---|---|---|
| 4,883,067 A | 11/1989 | Knispel et al. |
| 5,092,835 A | 3/1992 | Schurig et al. |
| 5,299,569 A | 4/1994 | Wernicke et al. |
| 5,365,939 A | 11/1994 | Ochs |
| 5,450,855 A | 9/1995 | Rosenfeld |
| 5,938,688 A | 8/1999 | Schiff |
| 6,066,163 A | 5/2000 | John et al. |
| 6,129,748 A | 10/2000 | Kamae |
| 6,205,359 B1 | 3/2001 | Boveja |
| 6,463,328 B1 | 10/2002 | John |
| 6,488,617 B1 | 12/2002 | Katz |
| 6,497,872 B1 | 12/2002 | Weiss et al. |
| 6,539,263 B1 | 3/2003 | Schiff |
| 6,594,524 B2 | 7/2003 | Esteller et al. |
| 6,678,548 B1 | 1/2004 | Echauz et al. |
| 7,209,787 B2 | 4/2007 | DiLorenzo |
| 7,282,021 B2 | 10/2007 | Rohan et al. |
| 7,400,927 B1 | 7/2008 | Litvin |
| 2002/0091419 A1 | 7/2002 | Firlik et al. |
| 2003/0004429 A1 | 1/2003 | Price |
| 2003/0097161 A1 | 5/2003 | Firlik et al. |
| 2003/0181954 A1 | 9/2003 | Rezai |
| 2004/0131998 A1 | 7/2004 | Marom et al. |
| 2005/0070778 A1 | 3/2005 | Lackey et al. |
| 2005/0070971 A1 | 3/2005 | Fowler et al. |
| 2005/0123526 A1 | 6/2005 | Shafer |
| 2005/0154425 A1 | 7/2005 | Boveja et al. |
| 2005/0256539 A1 | 11/2005 | George et al. |
| 2006/0058853 A1 | 3/2006 | Bentwich |
| 2006/0241718 A1 | 10/2006 | Tyler et al. |
| 2007/0066996 A1 | 3/2007 | Katzman et al. |

OTHER PUBLICATIONS

Roth, et al., "A Coil Design for Transcranial Magnetic Stimulation of Deep Brain Regions," Journal of Clinical Neurophysiology, 19(4):361-370 (2002).

INTEGRATED SYSTEM AND METHOD FOR TREATING DISEASE USING COGNITIVE TRAINING AND BRAIN STIMULATION AND COMPUTERIZED MAGNETIC PHOTOELECTRIC STIMULATOR (CMPES)

BACKGROUND OF THE INVENTION

Various functional and structural central nervous system (CNS) imaging instrumentations are known in the art, including inter alia Magnetic Resonance Imaging (MRI), Functional Magnetic Resonance Imaging (f-MRI), Positron Emission Tomography (PET) and Single Photon Emission Computerized Tomography (SPECT).

Various cognitive diagnostic techniques are known in the art including inter-alia Stroop Color Task, Navon Global Local Paradigm, Dimensional Meaning Profile, as well as various memory, intelligence, language, personality tests, cognitive-affective measurement tools, and tests for locating brain region deficiency, e.g., frontal-temporal deficiency.

Various non-invasive brain neuronal stimulation techniques are known in the art, including inter alia, Transcranial Magnetic Stimulation (TMS), and Deep TMS (Roth Y, Zangen A, Hallett M.: "A coil design for transcranial magnetic stimulation of deep brain regions", *J Clin Neurophysiol.* 2002 August; 19 (4):361-70).

SUMMARY OF THE INVENTION

The present invention provides an integrated system and method for treatment of various diseases, including psychiatric, mental, brain and bodily disorders, which preferably combines personalized brain stimulation together with appropriate personalized cognitive training, and which iteratively fine-tunes this treatment by monitoring specific cognitive and brain functions in response to treatment. A preferred embodiment of the present invention is the Integrated Cognitive Neuronal Stimulation (ICONS) system, which is described hereinbelow.

There is thus provided in accordance with a preferred embodiment of the present invention a medical device for treatment of a disease including: a non-invasive brain stimulator operative to selectively stimulate at least one region of a brain of a patient, which at least one region is associated with the disease; and a cognitive stimulator operative to stimulate at least one cognitive feature in the patient, which the at least one cognitive feature is associated with the disease.

There is further provided in accordance with another embodiment of the present invention a medical device wherein the medical device also includes an analyzer operative to modulate operation of the medical device based at least in part on comparison of a measurement of a property in a patient to a norm of the property, which property is one of the following items: a localized brain feature and a cognitive feature.

There is yet further provided in accordance with another embodiment of the present invention a medical device wherein the medical device also includes a feedback modulator operative to modulate operation of the medical device based at least in part on detection and analysis of alteration of a property following operation of the medical device, which property is one of the following items: a localized brain feature and a cognitive feature.

There is additionally provided in accordance with a preferred embodiment of the present invention a method of the therapy for a disease, the method including: stimulating at least one region of a brain of a patient, which at least one region is associated with the disease; and stimulating at

DETAILED DESCRIPTION OF THE DRAWINGS

Figure 1:
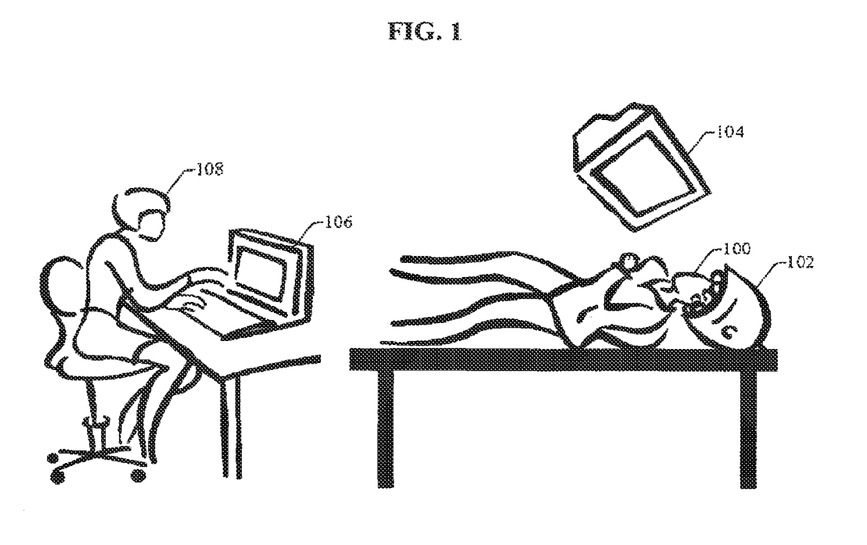
FIG. 1 is a simplified illustration of a usage of a medical device constructed and operative in accordance with a preferred embodiment of the present invention.

Reference is now made to FIG. 1, which is a simplified illustration of a usage of a medical device constructed and operative in accordance with a preferred embodiment of the present invention.

An important aspect of the present invention is the concept of integrating external neuronal stimulation of the brain, together with at least one cognitive feature in the patient, which the at least one cognitive feature is associated with the disease.

There is moreover provided in accordance with another embodiment of the present invention a method of the therapy for a disease wherein the method also includes: comparing a measurement of a property in property in a patient to a norm of the property, which property is one of the following items: a localized brain feature and a cognitive feature; and wherein the comparing modulates at least one of the following: the stimulating at least one region of a brain of a patient and the stimulating at least one cognitive feature in the patient.

There is further provided in accordance with another embodiment of the present invention a method of the therapy for a disease wherein the method also includes: analyzing alteration of a property following operation of the medical device, which property is one of the following items: a localized brain feature and a cognitive feature; and wherein the analyzing modulates at least one of the following: the stimulating at least one region of a brain of a patient and the stimulating at least one cognitive feature in the patient.

There is yet further provided in accordance with another embodiment of the present invention a medical device for treatment of a disease containing an electromagnetic stimulator and a laser stimulator and operative to induce a magnetic photo-electric stimulation which selectively stimulates at least one region of a brain of a patient, which at least one region is associated with the disease.

There is additionally provided in accordance with another embodiment of the present invention a method of therapy for a disease, the method consisting of: electromagnetically stimulating at least one region of a brain of a patient, which at least one region is associated with the disease; and laser stimulating the at least one region of a brain of a patient by means of at least one laser beam; and wherein the electromagnetically stimulating and the laser stimulating cause a magnetic photo-electric stimulation, e.g., cognitive training, that causes internal stimulation of the brain. Another important aspect of the present invention is the concept of patient-specific brain stimulation, which is based at least in part on a comparison of neuronal function and structure of a brain of a patient, and cognitive properties of a patient to a norm of these brain and cognitive properties in a control population. Yet another important aspect of the present invention is the concept of patient-specific brain stimulation, which is based on an iterative comparison of changes in brain-function and in cognitive properties, in response to treatment.

FIG. 1 illustrated a patient 100 being treated by an Integrated Cognitive Neuronal Stimulation (ICONS) system, constructed and operative in accordance with a preferred embodiment of the present invention, and which is further described hereinbelow with reference to FIGS. 2-4. As depicted by FIG. 1, the ICONS system preferably comprises of a brain stimulator and device 102, a cognitive stimulator and assessment device 104, an integrated treatment controller device 106, and optionally a human operator 108.

In accordance with a preferred embodiment of the present invention the brain stimulator and imaging device 102 is a medical device capable of selectively stimulating various regions of the brain, either excitatory or inhibitory stimuli. Various such devices are known in the art, including inter alia various Magnetic Photo-Electric Stimulator (MPES) devices, Transcranial Magnetic Stimulation (TMS) and Deep TMS devices.

In accordance with another preferred embodiment of the present invention, the brain stimulator and imaging device 102 is a medical device that stimulates various regions of the body, thus stimulating the brain indirectly, i.e., stimulating different organs of the body, thereby causing these organs to transmit neuronal impulses which stimulate regions of the brain.

In accordance with yet another preferred embodiment of the present invention, the brain stimulator and imaging device is also capable of functional and or structural imaging the brain. Imaging may be performed using various functional and structural CNS imaging instrumentations that are known in the art, including inter alia Magnetic Resonance Imaging (MRI), Functional Magnetic Resonance Imaging (MRI), Positron Emission Tomography (PET) and Single Photon Emission Computerized Tomography (SPECT).

It is appreciate that while FIG. 1 depicts both the brain stimulation and the brain imaging functionality as being performed by the brain stimulator and imaging device 102, this is not meant to be limiting: the brain imaging functionality may be performed by a physically separate instrument, which is a separate component of the ICONS device of the present invention, or the ICONS device may not include a brain imaging component.

In accordance with a preferred embodiment of the present invention the cognitive stimulator and assessment device 104 is a computer having a computer monitor and optionally a user-input device, such as a keyboard or a microphone, and which runs a computer program that causes display of cognitive stimuli on the computer monitor and accepts responses of the patient 100 to these stimuli. The cognitive stimulator and assessment device 104 is operative to perform specific cognitive stimulation, i.e., cognitive training, which is beneficial to the treatment of the patient 100, and is optionally also operative to assess the cognitive features of the patient 100, both at the start of the treatment as well as in response to the treatment.

The integrated treatment controller device 106 is a computer running a computer program, which computer program is constructed and operative to control the brain stimulator and imaging device 102, and the cognitive stimulator and assessment device 104. Operation of the integrated treatment controller device 106 is further described hereinbelow with reference to FIGS. 2 and 4.

Figure 2:
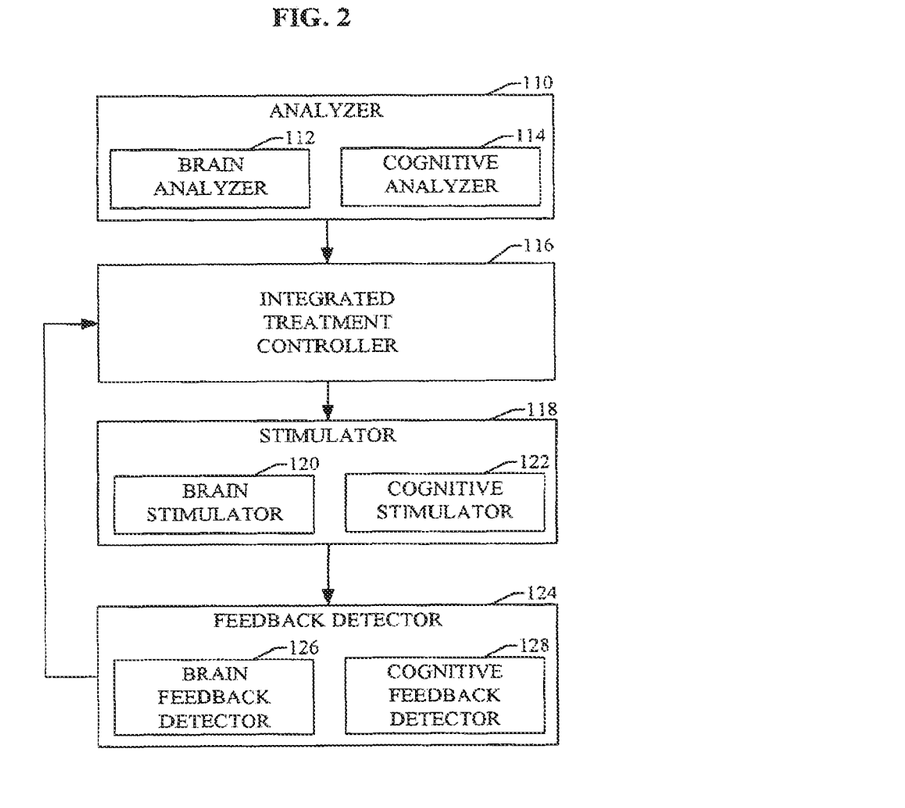
FIG. 2 is a simplified block diagram illustrating a design of a medical device constructed and operative in accordance with a preferred embodiment of the present invention.

Reference is now made to FIG. 2, which is a simplified block diagram illustrating a design of an Integrated Cognitive Neuronal Stimulation (ICONS) system constructed and operative in accordance with a preferred embodiment of the present invention.

Treatment of the patient 100 (FIG. 1) by the ICONS system of the present invention preferably begins by action of an analyzer 110, which preferably comprises a brain analyzer 112 and a cognitive analyzer 114. The analyzer is operational to assess localized brain properties, such as function or structure, and cognitive features, both of the patient 100, in comparison to a norm of these properties and features.

The brain analyzer 112 analyzes functional and structural brain properties of the patient 100 in comparison to a norm of these properties. Imaging may be performed using various functional and structural CNS imaging instrumentations that are know in the art, including inter alia Magnetic Resonance Imaging (MRI), Functional Magnetic Resonance Imaging (f-MRI), Positron Emission Tomography (PET) and Single Photon Emission Computerized Tomography (SPECT). Operation of the brain analyzer 112 is further elaborated hereinbelow with reference to FIG. 2A.

The cognitive analyzer 114 analyzes cognitive properties of the patient 100 in comparison to a norm of these properties. Cognitive analysis may be performed by a computer having a computer monitor and an input device and running a computer program which displays cognitive stimuli and measures responses of the patient 100 to these stimuli. The cognitive analyzer preferably utilizes at least one of various cognitive diagnostic techniques known in the art such as Stroop Color Task, Navon Global Local Paradigm, Dimensional Meaning Profile, various memory, intelligence, language, personality tests, cognitive-affective measurement tools, and tests for locating brain region deficiency in a disease state, such as in patients suffering from depression. Operation of the cognitive analyzer 114 is further elaborated hereinbelow with reference to FIG. 2B.

An integrated treatment controller 116 is a computer program, which receives as input the results of analysis of the analyzer 110, and based at least in part on these analysis results, computes and determines the appropriate, personalized, brain and cognitive stimuli for a patient 100. Operation of the integrated treatment controller 116 is further elaborated hereinbelow with reference to FIG. 4.

A stimulator 118 is a medical device, preferably comprising a brain stimulator 120 and a cognitive stimulator 122, which receives as input personalized brain and cognitive stimuli, calculated by the integrated treatment controller 116, and generates and applies these stimuli to the patient 100.

According to a preferred embodiment of the present invention the brain stimulator 120 is a medical device capable of selectively stimulating various regions of the brain, either excitatory or inhibitory stimuli. Various such devices are known in the art, including inter alia various Transcranial Magnetic Stimulation (TMS), and Deep TMS devices. In a preferred embodiment of the present invention, the brain stimulator 120 functionality may be achieved by a Computerized Magnetic Photo-Electric Stimulator (CMPES) device of the present invention, described hereinbelow with reference to FIG. 5.

In accordance with another preferred embodiment of the present invention, the brain stimulator and imaging device 102 is a medical device that stimulates various regions of the body, thus stimulating the brain indirectly, i.e., stimulating different organs of the body, thereby causing these organs to transmit neuronal impulses which stimulate regions of the brain.

In accordance with a preferred embodiment of the present invention the cognitive stimulator 122 is a computer having a computer monitor and optionally a user-input device, such as a keyboard or a microphone, and which runs a computer program that causes display of cognitive stimuli on the computer monitor and accepts responses of the patient 100 to these stimuli. The cognitive stimulator 122 is operative to perform specific cognitive stimulation, i.e., cognitive training, which is beneficial in treating a medical disease or condition of the patient 100. Such cognitive stimulation includes various cognitive tests and stimulations known in the art, such as Stroop Color Task, Navon Global Local Paradigm, Dimensional Meaning Profile, as well as various memory, intelligence, language, personality tests, cognitive-affective measurement tools, and tests for locating brain region deficiency, e.g., frontal temporal deficiency.

An important aspect of the present invention is a concept that cognitive training, when performed in conjunction with neuronal stimulation of the brain, improves the plasticity of the brain, and hence is synergistic to the neuronal stimulation of the brain.

A feedback detector 124 is a sensor device comprising a brain feedback detector 126 and a cognitive feedback detector 128, which iteratively measures changes in brain and cognitive parameters in response stimulation of the stimulator 118, and reports these changes to the integrated treatment controller 116. Based on the feedback data provided by the feedback detector 124, the integrated treatment controller 116 may modify its instructions to the stimulator 118, as to the type and intensity of the neuronal and cognitive stimuli to be applied to the patient 100.

The brain feedback detector 126 is a device operative to measure changes in functional and structural brain properties of the patient 100 in response to stimulation of the stimulator 118. Measurement may be performed using devices known in the art such as a Magnetic Resonance Imaging (MRI), Functional Magnetic Resonance Imaging (f-MRI), Positron Emission Tomography (PET) or Single Photon Emission Computerized Tomography (SPECT).

The cognitive feedback detector 128 is a device operative to measure changes in cognitive properties of the patient 100 in response to stimulation of the stimulator 118. Cognitive analysis may be performed by a computer having a computer monitor and an input device and running a computer program which displays cognitive stimuli and measures responses of the patient 100 to these stimuli. The cognitive analyzer preferably utilizes at least one of various cognitive diagnostic techniques known in the art such as Stroop Color Task, Navon Global Local Paradigm, Dimensional Meaning Profile, various memory, intelligence, language, personality tests, cognitive-affective measurement tools, and tests for locating brain region deficiency, e.g., frontal temporal deficiency.

Figure 3A:
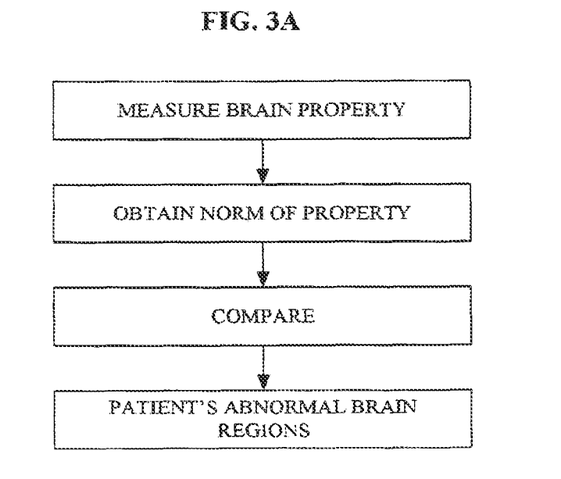
FIG. 3A is a simplified flowchart illustrating operation of a brain analyzer constructed and operative in accordance with a preferred embodiment of the present invention.

Reference is now made to FIG. 3A, which is a simplified flowchart illustrating operation of a brain analyzer 112 of FIG. 2, constructed and operative in accordance with a preferred embodiment of the present invention.

The brain analyzer 112 measures a localized brain property in the patient 100. The localized brain property may be a structural property or a functional property, and is preferably obtained by various neuro-imaging devices known in the art, such as Magnetic Resonance Imaging (MRI), Functional Magnetic Resonance Imaging (f-MRI), Positron Emission Tomography (PET) or Single Photon Emission Computerized Tomography (SPECT).

A norm of the localized brain property measured in the previous step is obtained. The norm is preferably calculated by performing the desired neuro-imaging of the previous step on a control group. The control group may be a group of healthy individuals, or a group of individuals diagnosed as having a specific disease, or a group of individuals diagnosed as not having a specific disease.

The measurement of the brain property in the patient 100 is compared to the norm of that property in the control group, so as to determine specific differences between the patient and the control group.

Based on the comparison of the previous step, abnormal brain regions of the patient 100 are determined. For example, by comparing the fMRI functional imaging results of the patient 100 to the fMRI results of a large group of healthy individuals, the regions of abnormality of the patient 100 may be determined. As an another example, if a patient 100 is known to suffer from autism, by comparing the functional imaging results of the patient 100 to those of a control group of patients diagnosed with autism, the specific regions of abnormality in the brain of the patient 100, which are likely to be associated with autism, are determined.

Determination of abnormal brain regions of the patient 100, which results from the previous step, is used by the integrated treatment controller 116 (FIG. 2), as further described hereinbelow with reference to FIG. 4.

It is appreciated that the sequence of the steps illustrated by FIG. 3A is provided as an illustration only, and is not meant to be limiting, and that these steps may be performed in a different sequence.

Figure 3B:
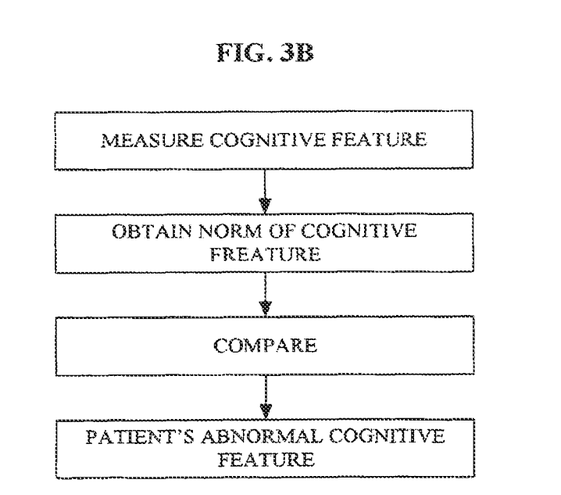
FIG. 3B is a simplified flowchart illustrating operation of a cognitive analyzer constructed and operative in accordance with a preferred embodiment of the present invention.

Reference is now made to FIG. 3B, which is a simplified flowchart illustrating operation of a cognitive analyzer 114 of FIG. 2, constructed and operative in accordance with a preferred embodiment of the present invention.

The cognitive analyzer 114 measures a cognitive feature in the patient 100. The cognitive feature is preferably measured by various cognitive tests known in the art, such as Stroop Color Task, Navon Global Local Paradigm, Dimensional Meaning Profile, various memory, intelligence, language, personality tests, cognitive-affective measurement tools, and tests for locating brain region deficiency, e.g., frontal-temporal deficiency.

A norm of the cognitive feature measured in the previous step is obtained. The norm is preferably calculated by performing the desired cognitive test of the previous step on a control group. The control group may be a group of healthy individuals, or a group of individuals diagnosed as having a specific disease, or a group of individuals diagnosed as not having a specific disease.

The measurement of the cognitive feature in the patient 100 is compared to the norm of that cognitive feature in the control group, so as to determine specific differences between the patient and the control group.

Based on the comparison of the previous step, abnormal cognitive features of the patient 100 are determined. For example, by comparing results of a cognitive test of the patient 100 to the results a large group of healthy individuals to that cognitive test, the abnormal test results of the patient 100 may be determined. As an another example, if a patient 100 is known to suffer from autism, by comparing results of the patient 100 in a cognitive test, to the results of a control group of patients diagnosed with autism to that cognitive test, the specific cognitive deficiencies of the patient 100, which are likely to be associated with autism, are determined.

Determination of abnormal cognitive features of the patient 100, which result from the previous step, is used by the integrated treatment controller 116 (FIG. 2), as further described herein below with reference to FIG. 4.

It is appreciated that the sequence of the steps illustrated by FIG. 3B is provided as an illustration only, and is not meant to be limiting, and that these steps may be performed in a different sequence.

Figure 4:
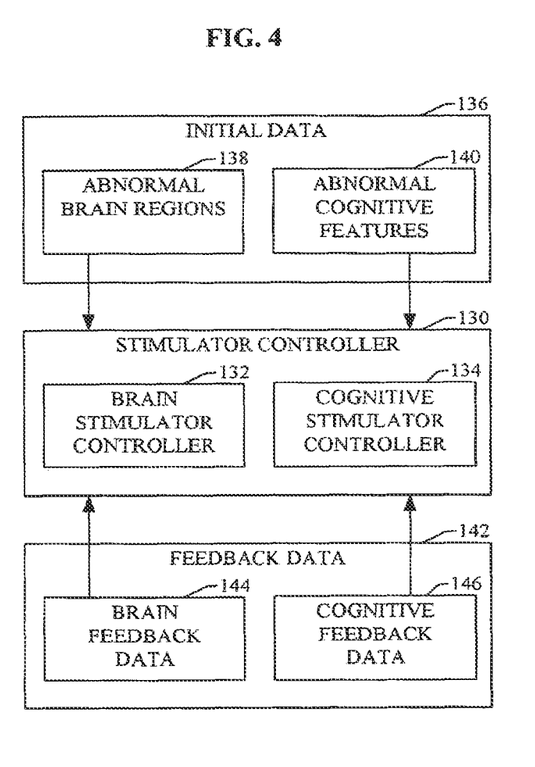
FIG. 4 is a simplified block diagram illustrating a design of an integrated treatment controller constructed and operative in accordance with a preferred embodiment of the present invention.

Reference is now made to FIG. 4, which is a simplified block diagram illustrating a design of an integrated treatment controller 116 of FIG. 2, constructed and operative in accordance with a preferred embodiment of the present invention.

The integrated treatment controller 116 comprises a stimulator controller 130, operative to control the stimulator 118 (FIG. 2), so as to personalize the neuronal and cognitive stimulation of the ICONS device of the present invention, adjusting it to an individual patient, such as the patient 100. The stimulator controller 130 comprises a brain stimulator controller 132, operative to control the brain stimulator 120 (FIG. 2), and a cognitive stimulator controller 134, operative to control the cognitive stimulator 122 (FIG. 2).

The stimulator controller 130 receives as input, initial data 136 comprising abnormal brain regions 138 and abnormal cognitive features 140, both of the patient 100. Based on this initial data 136, the stimulator controller 130 determines the neuronal and cognitive stimuli appropriate for an individual patient. Abnormal brain regions 132 are produced by operation of the brain analyzer 112 (FIG. 2), described hereinabove with reference to FIG. 3A. Abnormal cognitive features 134 are produced by operation of the cognitive analyzer 114 (FIG. 2), described hereinabove with reference to FIG. 3B.

The stimulator controller 130 also receives as additional input feedback data 142 comprising brain feedback data 144 and cognitive feedback data 146, both of the patient 100. Brain feedback data 144 is produced by operation of the brain feedback detector 126 (FIG. 2), and cognitive feedback data 146 is produced by operation of the cognitive feedback detector 128 (FIG. 2).

The feedback data 142 is an optional aspect of the present invention, allowing fine-tuning of the operation of the stimulator 118, and is preferably generated and passed on to the stimulator controller 130, iteratively, during the process of treatment. Alternatively it may take place intermittently, between treatment sessions, or at the end of treatment.

Figure 5:
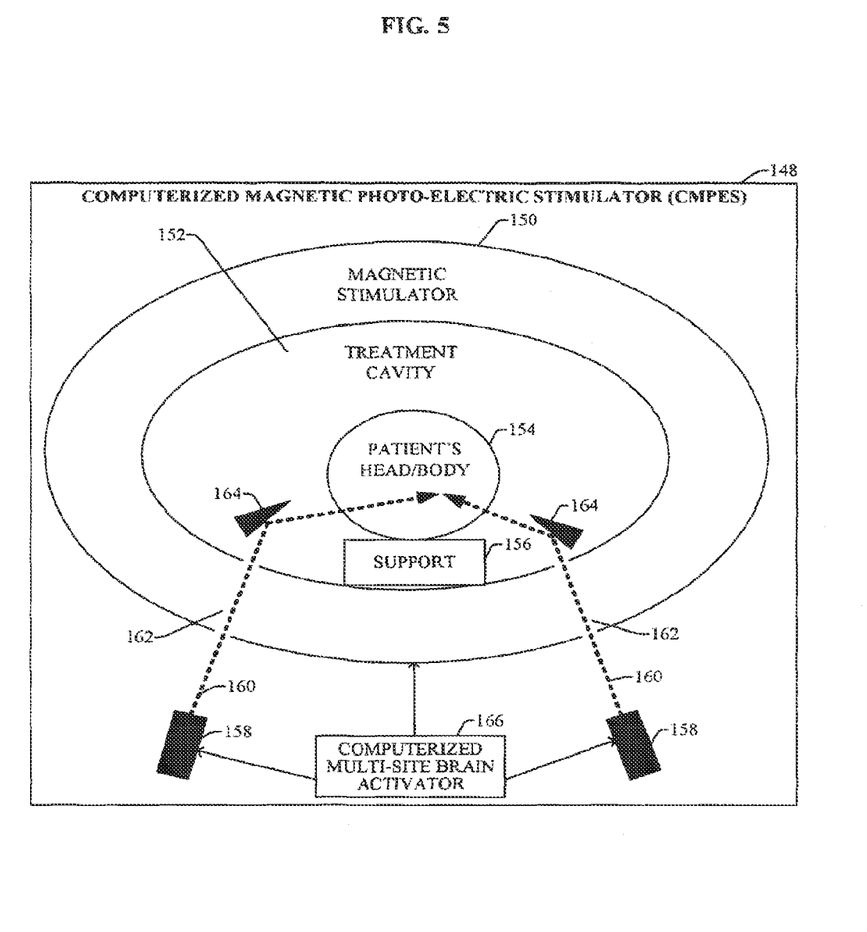
FIG. 5 is a simplified illustration of a Computerized Magnetic PhotoElectric Stimulator constructed and operative in accordance with a preferred embodiment of the present invention.

Reference is now made to FIG. 5, which is a simplified illustration of a Computerized Magnetic Photo-Electric Stimulator (CMPES), constructed and operative in accordance with a preferred embodiment of the present invention.

A Computerized Magnetic Photo-Electric Stimulator (CMPES) 148 is a device capable of therapeutically stimulating an organ of a patient, such as a head of a patient, preferably applying a combination of an electromagnetic stimulation together with a laser stimulation, thereby triggering a therapeutic photo-electric effect.

The Computerized Magnetic Photo-Electric Stimulator (CMPES) 148 comprises a magnetic stimulator 150, which is preferably a concentric hollow device capable of creating an electromagnetic stimulation.

The magnetic stimulator 150 surrounds a treatment cavity 152, in which the patient's head/body 154, which is to be treated, is placed. An optional support 156, may support the patient's head/body 154 in a proper location within the treatment cavity 152, and relative to the magnetic stimulator 150.

The Computerized Magnetic Photo-Electric Stimulator (CMPES) 148 further comprises at least one laser generator 158, which emits a respective at least one laser beam 160. The at least one laser generator 158 may be located inside the treatment cavity 152, or may be located outside thereof, emitting the at least one laser beam 160 through an optional at least one laser channel 162.

An at least one deflecting mirror 164 may be utilized to direct the at least one laser beam 160 to the desired specific location in the patient's head/body 154 which needs stimulation.

A computerized multi-site brain activator 166 controls the at least one laser generator 158, and the magnetic stimulator, and optionally the at least one deflecting mirror 164, so as to apply an integrated magnetic photoelectric stimulation.

It is appreciated that applying a plurality of the at least one laser beams 160, allows specific stimulation of an exact three-dimensional location within the patient's head/body 154.

It is further appreciated, that the combination of a magnetic stimulation generated by the magnetic stimulator 150, together with a laser stimulation caused by the at least one laser generator 158 causes a synergistic magnetic photo-electric stimulation.

The following description may be useful in further understanding the present invention and different possible embodiments thereof. Given extensive documentation of the localization of various Neuropsychological illnesses to specific brain-deficient (structural or functional) regions, and research indicating the "plasticity" of cognitive, affective and behavioral aspects following stimulation of corresponding neurological sites, the provisional patent outlines a novel integrative Clinical-therapeutic application of an individual-based brain stimulation of (functional/structural) deficient brain regions that is coupled with specific plasticity-based cognitive behavioral training methodologies that are geared towards improving the cognitive, affective, behavioral or bodily function (or condition) of the individual (as measured through localized brain functional/structural measurements and cognitive-behavioral or medical performance/condition measurements).

The present invention comprises of the following plasticity-based principles:

IDENTIFICATION OF INDIVIDUAL-BASED BRAIN-DEFICIENT REGIONS OF NEUROPSYCHOLOGICAL/ NEUROLOGICAL OR (ANY OTHER TYPE OF) BODILY AILMENT/DISEASE: A utilization of various (existing or prospective) measurement methodologies that can identify localized (functional or structural) brain deficient regions, relative to the normal population. The emphasis here is on the ability to localize—and statistically qualify—individual-based deviations in functional or structural properties of specific brain regions (relative to the normal-healthy population). An example for such (existent) instrumentation would be: Magnetic Resonance Imaging (MRI), Functional Magnetic Resonance Imaging (f-MRI), Positron Emission Tomography (PET), Single Photon Emission Computerized Tomography (SPECT), etc., when coupled with sophisticated cognitive-behavioral (or any other clinically specific) deviant performance measurement. It is to be emphasized here that this integrative therapeutic methodology capitalizes on the integration of specific cognitive/behavioral (or other clinical) measurements of deficient performance/capabilities of any particular Clinical population—as coupled with accurate brain-deficient (structural/functional) mapping—and powerful statistical deviation analysis of the (examined) individual relative to the "normal population".

UTILIZATION OF NEUROPSYCHOLOGICAL/NEUROLOGICAL/BODILY DISEASE SPECIFIC COGNITIVE-BEHAVIORAL/MEDICAL/PHYSIOLOGICAL TASK THAT BOTH QUANTIFIES IMPAIRED PERFORMANCE AND ASSISTS IN IDENTIFYING THE DEFICIENT BRAIN REGIONS (THROUGH BRIAN MAPPING, DISCUSSED ABOVE AND/OR WITH THE PROPOSED CMPES TECHNOLOGY): Usage of various Cognitive-Behavioral or Medical/Physiological tests or tasks that specifically identify the behavioral or cognitive/affective deficiency of each Clinical population. Among these tasks are included cognitive tasks/measurements such as: the Stroop Color-Task, Navon Global-Local Paradigm, various Memory, Intelligence, Language, frontal-temporal (or any other specific brain region) deficiency, various personality, cognitive-affective measurement tolls, but also prospective tests/tasks that specifically activate/measure the deficient brain/bodily illness/deficiency. An example for the ability of this integrative therapeutic tool to measure even the brain correlates (or tracers) of bodily illnesses is the utilization of Kreitler & Kreitler's Dimensional Meaning Profile—which was shown to cognitively distinguish between the performance of Ovarian Cancer patients, AIDS (and other clinical populations), and even between different professions (which in turn may be associated with particular health risks/deficiencies). The ability to identify and categorize a very wide range of illnesses/ailments—both Neuropsychological/Neurological and/or Bodily diseases—on the basis of specific Cognitive-Behavioral tasks/measurements, which can identify specific Neurological/Brain (structural or functional) deficiencies has far reaching implications and applications. Thus, for instance it is claimed that any (existing or prospective) Neuropsychological/Neurological or Bodily illness may be localized to a specific pattern of deficient (single- or multi-site localized) brain deficiency (relative to the normal healthy population), which then affords itself (through the proposed statistical brain imaging measurements) to an individual-based stimulation (e.g., excitatory or inhibitory) of those deficient brain regions, thereby significantly improving both performance and clinical condition (of the specific ailment). This is particularly true (for both Neuropsychological and Bodily Ailments Diseases) as there is ample scientific evidence suggesting that the brain not only serves as the "central executive control" of the nervous, immunological, endocrine (and practically all other systems and functions in the body), but also possesses extraordinary "plasticity" capabilities (both in terms of neural regeneration and in terms of effectively affecting the homeostasis of the body). Hence, this novel introduction of Cognitive-Behavioral tasks/measurements (and/or Physiological/Medical tasks/measurements) that can identify the specific brain-deficient localizations that are characteristic of any Neuropsychological/Medical Clinical Disease (in conjunction with the abovementioned brain mapping of individual-based deficient localizations measurements) offers a highly potent means of identifying and then stimulating these Illness-specific brain regions. It may be added here, that as part of the novel CMPES technology, the application of these Cognitive/Behavioral/Medical testing relating to the specific deficiencies that are characteristic of any Neuropsychological/Medical Disease/Ailment, would have an important application, not just in stimulating (e.g., activating or suppressing) specific brain regions, but also targeting such functional/structural deficient areas in the body (through electromagnetic stimulation of the deficient localization).

(SINGLE- OR MULTI-SITE) STIMULATION (E.G., EXCITATION OR SUPPRESSION) OF IDENTIFIED (FUNCTIONAL OR STRUCTURAL) DEFICIENT BRAIN-REGIONS (AND IN THE CMPES—ANYWHERE IN THE BODY): Here, the intent is to employ existing and/or novel Brain Stimulation methodologies (such as the CMPES) that allow for single- or multi-site excitatory or inhibitory stimulation of (functional or structural) deficient brain regions (all throughout the brain and nervous system, or throughout the Body, for the CMPES). Based on the identification of specific Brain (or bodily) deficient regions (with the combination of specific Cognitive-Behavioral/Medical tasks/tests and in conjunction with Brain mapping of these deficiencies), there will be an (excitatory or inhibitory) stimulation of these deficient regions, which is hypothesized to lead to a significant improvement in both (cognitive/behavioral/physiological) performance and its corresponding (neurological or medical) activity/health. Part of the novelty of this therapeutic integrative application has to so with the fact that for any Neuropsychological/Medical Clinical Disease/condition there should be an effective therapeutic intervention, through the appropriate stimulation of the (Cognitive-Behavioral/Medical tasks' identified deficient) brain/body regions, which relies on the well-documented plasticity and capabilities of both the functional and structural regenerative aspects of the brain's operation (in controlling both neurochemical activity and bodily functions and homeostasis).

PLASTICITY-BASED TRAINING METHODOLOGIES OF COGNITIVE BEHAVIORAL (OR PHYSIOLOGICAL/MEDICAL) DEFICIENT CAPABILITIES (IN CONJUNCTION WITH THE STIMULATION OF THE CORRESPONDING NEURAL/BODILY DEFICIENT LOCALIZATIONS): Finally, the proposed Integrative Therapeutic Application calls for a powerful synergy between the stimulation of Brain (or CMPES' bodily) "deficient" (e.g., hypo- or hyper-activation/function/structure) regions and the direct training of these brain (or bodily) "deficient" capabilities through (existing or novel) training methodologies (such as mnemonic, semantic, reasoning, mathematical, physical, etc.) that specifically improve the functional (or structural capabilities) of these deficient Brain/Cognitive-Behavioral/Physiological/Medical Capabilities. A good example for this principle is the utilization of various (existing or novel) short-term memory-training methodologies applied in conjunction with Brain activation of the specific deficient regions associated with Alzheimer's (initial) loss of short-term memory functions (as identified through the Cognitive-Behavioral tests). It is worthwhile noting that this combination of neurophysiological brain stimulation (or CMPES bodily stimulation), along with specific plasticity-based training methodologies, is especially powerful, given extensive knowledge of the regenerative processes associated with brain stimulation (both in terms of function and dendritic growth), which also appears to facilitate the effectiveness of various cognitive behavioral interventions (as in the case of the enhanced capability to "erase" traumatic memories in PTSD through a combination of specific psychological manipulation and stimulation of the affected brain regions).

The present invention may further be clarified by the following steps:

STEP 1: IDENTIFICATION OF (EXISTING OR PROSPECTIVE) NEUROPSYCHOLOGICAL/NEUROLOGICAL BRAIN (OR ALSO CMPES' BODILY/MEDICAL) DEFICIENCY THROUGH SPECIFIC COGNITIVE-BEHAVIORAL/PHYSIOLOGICAL TASKS/TESTS/MEASUREMENTS WITH CONCURRENT BRAIN IMAGING: These allow us to localize the deviant pattern of brain (or bodily) activation (on an individual-basis, as well as collectively for all patients suffering from a specific Disease/condition).

STEP II: BRAIN (OR BODILY) STIMULATION OF DEFICIENT (FUNCTIONAL OR STRUCTURAL) REGIONS: through a sophisticated individual based statistical analysis of deficient brain (or bodily) activity/structure, relative to the normal brain (or body). The primary advantage here is both the fact that we can individually "tailor" the brain (bodily) stimulation according to the specific localization/s of the deficiency and their precise 'deficiency value' relative to the "healthy norm" (as established statistically) (e.g., adjust the necessary excitatory or inhibitory stimulation in intensity, duration and recurrency, based on the particular pattern of individual deficiency), as well as the temporal-spatial accuracy of the application of the corrective stimulation (i.e., with the brain/bodily mapping of deficiencies tied almost simultaneously to the deliverance of individually tailored treatment).

STEP III: PLASTICITY-BASED TRAINING OF SPECIFIC DEFICIENT BRAIN (OR BODILY) REGIONS: Identification of (existent or prospective) training methodologies that specifically address the Cognitive-Behavioral/Medical deficiency/ies, that would be administered in conjunction with the stimulation of the deficient Brain/Bodily regions, to maximize the plastic changes in brain activation (functionally and structurally) and general homeostasis controlling capabilities of bodily functions/condition.

STEP IV: MEASUREMENT OF COGNITIVE-BEHAVIORAL/MEDICAL IMPROVEMENT: Both through localized (functional structural or other) brain mapping and corresponding Clinical Performance/condition. This module also allows for an STEP V: ASSESSMENT AND REAPPLICATION/ADJUSTMENT OF BRAIN/BODILY STIMULATION—UNTIL (PARTIAL OR FULL) RECOVERY OR IMPROVEMENT IN PERFORMANCE/CLINICAL CONDITION: Given the Homeostasis capabilities of plasticity-based regeneration of functional/structural brain capabilities, the application of both localized stimulation of deficient brain (or bodily) regions that is coupled with rigorous (and possibly repetitive) plasticity-based specific training (for these deficient Cognitive-Behavioral/Medical capabilities) may very well lead to a dynamic change in the individual-based performance as well as brain/bodily deficient regions/functions. Therefore the continuous measurement feedback of improved functional/structural capabilities can be interactively modulated until a (partial or full) remediation/normalcy results.

A Computerized Magnetic Photo-Electric Stimulator (CMPES)

In accordance with another preferred embodiment of the present~invention, a Computerized Magnetic Photo-Electric Stimulator (CMPES) is described. The CMPES is a novel apparatus that utilizes a strong magnetic field applied to either the entire (or parts of) the human brain and/or the human body (or parts of it), in conjunction with localized laser beams, which together produce localized electrical stimulation of the "deficient" (over- or under-activated) brain/bodily regions, thereby improving the functional, structural or medical/health of any diseased/deficient organ, system, or entire body.

Based on the well-known photoelectric effect, and the interchangeability of electro-magnetic energy, the novel CMPES device—which will also consist of advanced statistical analysis of brain/body imaging of "deficient" (e.g., hypo- or hyper-activation) on an individual-based level (as well as relative to specific Clinical Diseases)—would allow for a computerized detection of single- or multiple- (structural or functional) deficient activation brain/bodily sites and "correct" this deficiency through the elicitation of electromagnetic current in those deficient regions.

The rationale for the hypothesized highly effective therapeutic effect of the CMPES is quite obvious in the case of brain deficiencies, due to the well-known (functional and structural) plasticity of neural activity following "corrective" (e.g., facilitative or inhibitory) electrical stimulation. Thus, for example research indicates that the application of corrective ECT or Transcranial Magnetic Stimulation (TMS) may eliminate epileptic seizures or disrupt deficient cognitive processing (as in the case of stimulating the left prefrontal cortex of Clinically Depressed Patients), as well as stimulate regenerative dendritic sprouting. Furthermore, given preliminary evidence that even regular cells may be characterized in terms of their "normal" or "deficient" electromagnetic or photonic emission imprint, it is reasonable to expect that an electromagnetic-photonic stimulation of specific regions that have been shown to be deviant in terms of their functional/structural patterns, may be greatly enhanced through this novel technology (including but not limited to therapeutic effects on cancerous cells, neural paralysis, endocrine functioning and, perhaps even at a cellular level, genetic treatment).

It is appreciated by persons skilled in the art that the present invention is not limited by what has been particularly shown and described hereinabove. Rather the scope of the present invention includes both combinations and subcombinations of the various features described hereinabove as well as variations and modifications which would occur to persons skilled in the art upon reading the specifications and which are not in the prior art.

The invention claimed is:

1. A method for treatment of Alzheimer's disease in a patient, comprising:
    stimulating at least one abnormal region of a brain of the patient with magnetic stimulation or with electric stimulation, using a non-invasive electromagnetic brain stimulator; and
    concurrently administering a cognitive stimulation associated with the abnormal brain region of the patient, using a computerized cognitive brain stimulator.

2. The method according to claim 1, wherein said method further comprises analyzing alteration of a localized brain feature or a cognitive feature following said stimulating and administering steps, and modulating at least one of the steps of stimulating at least one abnormal region of a brain of the patient or administering a cognitive stimulation.

3. The method for treatment according to claim 1, wherein said stimulating step comprises stimulating at least one abnormal region of a brain of the patient with magnetic stimulation wherein said magnetic stimulation is carried out using a transcranial magnetic stimulator (TMS) or a repetitive transcranial magnetic stimulator (rTMS).

4. The method for treatment according to claim 1, wherein said administering step comprises administering memory-related stimulation to the patient.

5. A method for treatment of a neurodegenerative disease in a patient, comprising:
    stimulating at least one region of a brain of the patient with magnetic stimulation or with electric stimulation, using a non-invasive electromagnetic brain stimulator, which at least one region is a specific brain region associated with said disease; and
    concurrently administering a memory-related cognitive stimulation associated with a specific brain region of the patient, using a computerized cognitive brain stimulator.

6. The method according to claim 5, wherein said method further comprises analyzing alteration of a localized brain feature or a cognitive feature following said stimulating and administering steps, and modulating at least one of the steps of stimulating at least one region of a brain of the patient or administering a cognitive stimulation.

7. The method for treatment according to claim 5, wherein said stimulating step comprises stimulating at least one region of a brain of an individual with magnetic stimulation wherein said magnetic stimulation is carried out using a transcranial magnetic stimulator (TMS) or a repetitive transcranial magnetic stimulator (rTMS).

\* \* \* \* \*